United States Patent [19]

Larkin

[11] Patent Number: 5,853,799
[45] Date of Patent: Dec. 29, 1998

[54] LIQUID METHYLTIN HALIDE COMPOSITIONS

[76] Inventor: William Albert Larkin, 38 Sylvania Ave., Avon by the Sea, N.J. 07717

[21] Appl. No.: 915,108

[22] Filed: Aug. 20, 1997

Related U.S. Application Data

[62] Division of Ser. No. 459,958, Jun. 2, 1995, Pat. No. 5,725,904.

[51] Int. Cl.$^6$ .................................... C23C 16/40
[52] U.S. Cl. ......................... 427/160; 427/166; 427/168; 427/169; 427/255.3; 427/226
[58] Field of Search ..................... 427/109, 110, 427/160, 166, 168, 169, 255.3, 226

[56] References Cited

U.S. PATENT DOCUMENTS

| 2,566,346 | 9/1951 | Lytle et al. | 117/54 |
| 4,130,673 | 12/1978 | Larkin | 427/255 |
| 4,144,362 | 3/1979 | Larkin | 427/226 |
| 4,187,336 | 2/1980 | Gordon | 428/34 |
| 4,254,017 | 3/1981 | Dworkin et al. | 260/45.75 |
| 4,293,594 | 10/1981 | Yoldas et al. | 427/107 |
| 4,530,857 | 7/1985 | Lindner | 427/314 |
| 4,547,400 | 10/1985 | Middleton et al. | 427/160 |
| 4,584,206 | 4/1986 | Sleighter | 427/109 |
| 4,731,256 | 3/1988 | Russo et al. | 427/109 |
| 4,731,462 | 3/1988 | Russo et al. | 556/105 |
| 5,004,490 | 4/1991 | Brown | 60/60.52 |
| 5,090,985 | 2/1992 | Soubeyrand et al. | 65/60.52 |
| 5,725,904 | 3/1998 | Larkin | 427/109 |

*Primary Examiner*—Michael Lusignan
*Assistant Examiner*—Timothy Meeks
*Attorney, Agent, or Firm*—Stanley A. Marcus; Nicholas J. DeBenedictis

[57] ABSTRACT

Liquid methyltin halide compositions and their use as intermediates in chemical synthesis and as precursors for forming tin oxide coatings on substrates are disclosed.

2 Claims, No Drawings

LIQUID METHYLTIN HALIDE COMPOSITIONS

This is a divisional of application Ser. No. 08/459,958 filed on Jun. 2, 1995, now U.S. Pat. No. 5,725,904.

BACKGROUND OF THE INVENTION

This invention relates to compositions of matter classified in the art of chemistry as organotin halides, more specifically as methyl tin halide containing compositions as well as methods for their preparation and use.

Methyltin halides such as monomethyltin trichloride and dimethyltin dichloride are solid materials at 24° C. This characteristic alone makes them unsuitable or uneconomical for many applications. For example, where the methyltin chlorides are to be used as chemical intermediates in the manufacture of esterification catalysts or stabilizers for halogenated polymers, they must first be dissolved in a suitable solvent, melted or pulverized to fine powders. Each of these modifications result in increased costs and reduced production efficiency. In like manner, when the methyltin halide is to be used as a coating precursor for the production of tin oxide coatings on glass or other substrates, most frequently through pyrolytic conversion to tin oxide, its solid, non-liquid nature requires that it be dissolved in a solvent or vaporized. Vaporization does not eliminate the handling problems associated with such solids, particularly when feeding the methyltin halide to the vaporization equipment. The vapors readily deposit solids, not only on the articles to be coated, but also on adjacent equipment walls and exhaust ducts of the coating equipment, resulting in the need for frequent shut downs to remove solids.

Introduction of solvents, such as alcohol or water to convert the methyltin chloride to liquid compositions which can be more easily handled, has the negative effect of diluting the active species.

Where the methyltin chloride is to be used as a chemical intermediate, such dilution increases transportation costs, reduces reactor volume efficiency and can increase corrosivity where water is used as the diluent.

When the methyltin chlorides are used for the production of tin oxide coatings on glass and other substrates by pyrolytic chemical vapor deposition, spraying or dipping, introduction of solvents to convert the solid methyltin chloride to easily handled liquid compositions, results in several significant deficiencies. The active species is diluted, requiring that a greater volume of material be used, resulting in increased pollution abatement costs. If organic solvents, such as alcohols are used, fire and explosion hazards increase, necessitating greater safety precautions and the installation of special fire and explosion suppressing equipment or the addition of oxygen diluting gasses, such as nitrogen. Further, introduction of excessive amounts of solvents, including water, can have a deleterious effect on the quality of the tin oxide coatings, most frequently seen as haze, loss of electrical conductivity or surface roughness. Solvent diluted compositions interfere with coating efficiency when a continuous bottle coating line is being started up. A long time is required before satisfactory coating is achieved, due to the need to overcome the cooling effect of the solvent in the coating hood. The result is a loss of initial production.

There are a great many U.S. patents which describe the use of organotin chlorides as chemical intermediates in the production of heat stabilizers for halogenated polymers, particularly, polyvinyl chloride; catalysts for urethane, esterification and condensation reactions and as precursors for tin oxide coatings on glass and other substrates to provide transparent electroconductive and infrared reflecting coatings, improve scratch resistance, and improve physical properties. Such coated glass is used in the construction of solar cells, automobile windshields, glass refrigerator doors, "Low-E" or IR reflective glass, and in electronic applications, to name a few.

U.S. Pat. No. 4,144,362—A method for coating glass using monoalkyltin trihalides.

The utility of organotins and inorganic tines as precursors for the production of stannic oxide coatings on glass is discussed. The superiority of monobutyltin trichloride, in this application, is disclosed and claimed.

U.S. Pat. No. 4,130,673—A process of applying tin oxide on glass using butyltin trichloride as the precursor.

This patent describes the usage of monobutyltin trichloride to deposit a tin oxide coating on glass by applying finely divided or vaporizable butyltin trichloride to a heated glass surface. The coated glass is coated with a natural wax or synthetic polymer to reduce the coefficient of friction.

U.S. Pat. No. 4,530,857—Glass container hot-end coating formulation and method of use.

Describes the use of "dopants" to prevent formation of solids in liquid organotin precursors for the depositions of stannic oxide coatings on hot glass. It is noted that the "dopants" would ordinarily be considered an impurity and do not contribute in any positive way to the coating process or the quality of the finished product. Although methyltin trichloride is mentioned as a precursor, it is not noted that this material is a solid, and therefore, would not benefit by the addition of the dopants.

U.S. Pat. No. 2,566,346—Electroconductive products and production thereof.

Describes the use of aqueous solutions of a tin compound and an ionizable fluoride to produce electroconductive glass articles.

U.S. Pat. No. 4,187,336—Non-iridescent glass structures.

This patent teaches coating constructions of specific composition and thickness to produce infrared reflective glass (windows) free of iridescence. One or more of the coatings may be stannic oxide.

U.S. Pat. No. 4,254,017—Organotin mercaptoalkanol esters containing sulfide groups.

Describes organotin compounds useful as PVC stabilizers which may be derived from organotin halides including: monomethyltin trichloride as the intermediate or starting material.

U.S. Pat. No. 4,731,462—Organotin compounds containing fluorine useful for forming fluorine doped tin oxide coatings.

Describes fluorine containing organotin compounds useful for producing doped tin oxide coatings. Monomethyltin trichloride and dimethyltin dichloride may be used as raw materials in the manufacture of the fluorine containing organotins.

U.S. Pat. No. 4,584,206—Chemical vapor deposition of a reflective film on the bottom surface of a float glass ribbon.

The patent describes a coating method in which organotin compounds may be used as precursors to tin oxide coatings.

U.S. Pat. No. 4,547,400—Method of making infrared reflective glass sheet.

Describes the use of a metallic oxide seal coat which does not form sodium chloride crystals. The seal coat and subsequent coatings may be tin oxide derived from organotin compounds as precursors.

U.S. Pat. No. 5,004,490—Method of making glass substrate coated with tin oxide.

Employs organotin alkoxides as tin oxide precursors to produce a thicker coating of tin oxide.

U.S. Pat. No. 4,293,594—Method for forming conductive transparent coatings on a substrate.

The substrate is a vitreous tubular member of predetermined dimensions (e.g. fluorescent light tube). The conductive coating is tin oxide derived from a precursor organotin halide compound.

OBJECT OF THE INVENTION

It is an objective of the present invention to provide novel, stable liquid methyltin chloride containing compositions useful as chemical intermediates and as precursors to tin oxide coatings on glass and other substrates.

One objective is to provide novel methyltin containing compositions useful on glass bottle coating lines, exhibiting high-efficiency during line start-up.

Another objective is to provide novel liquid tin oxide precursor compositions comprising methyltin chlorides exhibiting faster deposition rates in chemical vapor deposition processes and greater efficiency than other organotin compositions and which may be recovered and recycled as liquid compositions using known techniques.

Another object of the invention is to provide novel methyltin chloride containing compositions which are easily handled liquids at ambient temperatures, typically 24° C.

SUMMARY OF THE INVENTION

The invention provides in a composition aspect, a composition liquid at 24° C. consisting essentially of a methyltin halide selected from monomethyltintrichloride, dimethyltindichloride or mixtures thereof and a liquid monoalkyltintrichloride.

The compositions of the invention have the inherent applied use characteristics of being easily handled intermediates for the production of other known organotin derivatives having utility inter alia as stabilizers for polymer organic substances.

The compositions of the invention are also easily handled precursors for the deposition of tin oxide coatings on glass and other substrates.

Use of the compositions of the invention provides the additional advantage of making available liquid compositions which because of the relatively low molecular weight of the methyltin halides in the compositions provide a higher percentage of tin per unit weight.

The compositions of the invention are easily handled liquids which can be transported and utilized economically.

The invention also provides in a process aspect an improved process for depositing tin oxide coatings on substrates wherein the improvement comprises the use of the composition aspects of the invention in such process.

The invention also provides in a second composition aspect, articles of manufacture produced by the process of the invention.

When used herein and in the appended claims, the term "consisting essentially of" does not exclude traces of moisture absorbed from the atmosphere and the various known adjuvants to prevent precipitation, improved shelf stability, lower corrosivity, improve IR reflectivity of deposited tin oxide, which may be added in small quantities (up to about 10% by weight) to the compositions of the invention without departing from the scope of the invention.

It does exclude, however, quantities of common solvents, including water and aqueous mixtures in the quantities significantly greater than 10% by weight normally used to solubilize methyl tin chlorides.

Although the compositions of the invention may be diluted with water, or other solvents, if desired, the term "consisting essentially of" contemplates the composition aspect of the invention being substantially free thereof.

DESCRIPTION OF THE INVENTION

The compositions of the invention are readily made by simply mixing the solid methyltin halide and the desired liquid alkyl tin halide and warming, if necessary, to effect solution.

Monomethyltin trichloride and dimethyltin dichloride, both of which are useful as precursors for coating compositions to deposit tin oxide coatings on glass and other substrates, and as precursors or intermediates for the manufacture of catalysts and polymer stabilizers, are difficult to handle, package, and transport solids at ambient temperature, typically 24° C.

Combining the solid monomethyltin trichloride and/or dimethyltin dichloride with liquid monoalkyltin trichlorides as described in examples 1 through 20 below, yields methyltin chloride containing compositions which are liquids at 24° C. Such liquid compositions are more easily handled, transported and utilized. Further, it has been demonstrated as shown in example 21 that the product of the invention exhibits a faster deposition rate and that the tin oxide coating exhibits a lower emissivity, both desirable characteristics, when compared to a standard, non-methyltin, organotin precursor for the deposition of tin oxide coatings on glass substrates.

For liquid compositions at 24° C. when monobutyltintrichloride is employed, the maximum amount of monomethyltin trichloride which may be present is 70 weight percent, the maximum amount of dimethyltin dichloride by itself in monobutyltin trichloride is 10 weight percent and in mixture with monomethyltin trichloride it is 15 weight percent. Concentrations in other liquid alkyltin halides will be of similar orders of magnitude and can be determined readily as taught herein.

The following examples further illustrate the best mode contemplated by the inventor for the practice of his invention.

EXAMPLES 1 THROUGH 20

In examples 1 through 20, the tin compounds used were all of commercial grade, having a purity of 95% or greater, the physical characteristics of each tin compound at 24° C. is shown.

| MMTC | Monomethyltin trichloride | Solid, MP 46° C. |
|------|---------------------------|------------------|
| MBTC | Monobutyltin trichloride | Liquid- |
| $M_2TC_2$ | Dimethyltin dichloride | Solid, MP 108° C. |
| MOTC | Monoctyltin trichloride | Liquid- |
| MPTC | Monophenyltin trichloride | Liquid- |
| $SNCl_2$ | Stannous Chloride | Solid, 248° C. |
| SnG | Stannous Glycoxide | Solid > 100° C. |
| $SnCl_4$ | Stannic Tetrachloride | Liquid- |
| SnO | Stannous Oxide | Solid > 100° C. |

Examples 1 through 20 were prepared by placing the tin compounds, in the weight percent ratios noted in Table I, into glass vials which were then capped and shaken for approximately 3 minutes. Temperatures were increased, as noted in Table I, to effect complete solution.

Examples 1 and 12, which shown complete solubility at 24° C. to 35° C. are most preferred. Examples 2, 3, 4, 5, 10 and 13, which shown partial solubility at 24° C. and complete solubility at 50° C., are also preferred. Examples 6, 7, 8, 9, and 14 illustrate that even at high levels of dimethyltin dichloride or mono-octyltin trichloride, liquid products are obtained below 100° C.

Examples 15 and 16 illustrate limitations of the invention to alkyltin compounds due to reaction or redistribution of monomethyltin trichloride with the aryltin compound, monophenyltin trichloride, resulting in an undesirable product.

Examples 17 through 20 illustrate further the limitations of the invention, due either to the insolubility of the tested inorganic tin compounds in the liquid mixture of organotin chlorides, or reaction of tintetrachloride with components of the organotin chlorides.

The stability of the liquid products was demonstrated by subjecting each to three freeze/thaw cycles. Complete solubility means that the liquid products were totally liquid after the freeze/thaw test. Partial solubility means that the major portion of the methyltin chloride was in solution and the balance dispersed in the monoalkyltin trichloride.

In addition to the accelerated freeze/thaw test, shelf stability tests, at ambient temperatures were conducted on the preferred composition, 50/50 weight/weight percent monomethyltin trichloride/monobutyltin trichloride for 24 months. No changes occurred in the samples after storage in a closed glass container.

and labeled CFB. The deposition rate and emissivity of the coated glass were determined by the same methods disclosed in U.S. Pat. No. 4,601,917 with the following results.

|      | Deposition Rate Angstroms Per Second | Emissivity |
|------|-------------------------------------:|-----------:|
| CFMB | 533                                  | .39        |
| CFB  | 461                                  | .41        |

The higher deposition rate for CFMB, approximately 15%, is desirable, as it results in thicker coatings within a fixed coating time.

The lower emissivity is also desirable and is partly due to coating thickness, 1951 Angstroms for the CFMB coated sample and 1837 Angstroms for the CFB coated sample. The appearance of the coated glass was the same for the CFMB and CFB coated samples. In pyrolytic chemical vapor deposition processes more rapid deposition also results in more rapid achievement of equilibrium conditions which reduces the reject rate on start up.

EXAMPLE 22

A thermal stabilizer for polyvinyl chloride can be prepared as described in "Organotin Compounds", Robert Ingham, Sanders Rosenberg and Henry Gilman, October 1960, Chemical Reviews, published by the American

TABLE 1

| Ex. # | \multicolumn{9}{c}{Tin Compound, Weight %} | | | | | | | | | Solubility at | | |
|---|---|---|---|---|---|---|---|---|---|---|---|---|
| | MMTC | MBTC | $M_2TC_3$ | MOTC | MPTC | $SnCl_3$ | SnO | SnG | $SnCl_4$ | 24° C. | 50° C. | 75° C. |
| 1 | 50 | 50 | | | | | | | | Complete | | |
| 2 | 70 | 30 | | | | | | | | Partial | Complete | |
| 3 | 60 | 40 | | | | | | | | Partial | Complete | |
| 4 | 37.5 | 50 | 12.5 | | | | | | | Partial | Complete | |
| 5 | 45 | 40 | 15 | | | | | | | Partial | Complete | Complete |
| 6 | | 50 | 50 | | | | | | | Insoluble | Partial | Complete |
| 7 | | 60 | 40 | | | | | | | Insoluble | Partial | Complete |
| 8 | | 67 | 33 | | | | | | | Insoluble | Partial | Complete |
| 9 | | 75 | 25 | | | | | | | Insoluble | Partial | Complete |
| 10 | | 80 | 20 | | | | | | | Insoluble | Complete | |
| 11 | | 90 | 10 | | | | | | | Partial | Complete | |
| 12 | 50 | | | 50 | | | | | | Partial | Complete (35° C.) | |
| 13 | 70 | | | 30 | | | | | | Partial | Complete | |
| 14 | 40 | | | 60 | | | | | | Partial | Partial | Complete |
| 15 | 60 | | | | 40 | | | | | Insoluble | Reaction | |
| 16 | 50 | | | | 50 | | | | | Partial | Reaction | |
| 17 | 50 | 25 | | | | 25 | | | | Insoluble | Insoluble | Insoluble |
| 18 | 25 | 50 | | | | | 25 | | | Insoluble | Insoluble | Insoluble |
| 19 | 25 | 50 | | | | | | 25 | | Insoluble | Insoluble | Insoluble |
| 20 | 25 | 50 | | | | | | | 25 | Reaction | — | — |

EXAMPLE 21

The composition of the preferred example 1,50 weight percent monomethyltin trichloride/50 weight percent monobutyltin trichloride, was further modified by the addition of 5 weight percent trifluoroacetic acid and 5 weight percent of methylisobutyl ketone and identified as CFMB. This material was then evaluated as a tin oxide precursor in the pyrolytic chemical vapor deposition process for coating glass, disclosed in U.S. Pat. No. 4,601,917. The equipment used and the procedures used are described in the same patent. As a control composition, monobutyltin trichloride modified by the addition 5 weight percent trifluoracetic acid and 5 weight percent methylisooctyl ketone was prepared Chemical Society, using the mixed methyltin chloride/monoalkyl tin trichloride solution of the invention. When a 50/50 weight/weight mixture of methyltin trichloride/monobutyltin trichloride is used as one of the raw materials, it is first neutralized with ammonium hydroxide to form a mixture of methyl stannoic acid and butyl stannoic acid, which can be purified, isolated and dried. Alternatively the mixed stannoic acids can be converted to a mixture of monomethyltin tris iso octyl mercapto acetate and monobutyltin tris iso-octyl mercapto acetate by reaction with a stoichiometric equivalent of iso-octyl mercapto acetate. The stabilizer is added to polyvinyl chloride at typically 1% to prevent degradation during thermal processing.

EXAMPLE 23

The purified, isolated and dried mixed methyl stannoic acid (anhydride)/butyl stannoic acid(anhydride) of example 22, is effective as an esterification catalyst. When used at 0.2% in a stoichiometric mixture of phthalic anhydride/iso-octanol, dioctyl phthalate is produced rapidly at low temperature.

The subject matter which application regards as is invention is particularly pointed out and distinctly claimed as follows:

1. An improved process for the pyrolytic deposition of a tin oxide coating on a substrate wherein the improvement comprises the use of a composition which is liquid at 24° C. consisting essentially of a methyl tin halide selected from the group consisting of mono methyl tin trichloride, dimethyl tin dichloride and mixtures thereof, and an alky tin trichloride which is liquid at 25° C. to deposit said tin oxide coating.

2. A process as defined in claim 1 wherein the coating deposited contains ingredients to provide reduced infrared emissivity.

* * * * *